United States Patent
Hoots et al.

(10) Patent No.: US 10,436,719 B2
(45) Date of Patent: Oct. 8, 2019

(54) METHOD OF MONITORING AND OPTIMIZING ADDITIVE CONCENTRATION IN FUEL ETHANOL

(71) Applicant: Nalco Company, Naperville, IL (US)

(72) Inventors: John E. Hoots, Batavia, IL (US);
Phillip E. Bureman, Olathe, KS (US);
Craig W. Myers, Lisle, IL (US)

(73) Assignee: Ecolab USA Inc., St. Paul, MN (US)

( * ) Notice: Subject to any disclaimer, the term of this patent is extended or adjusted under 35 U.S.C. 154(b) by 169 days.

(21) Appl. No.: 14/679,575

(22) Filed: Apr. 6, 2015

(65) Prior Publication Data

US 2015/0212007 A1 Jul. 30, 2015

Related U.S. Application Data

(63) Continuation of application No. 12/143,400, filed on Jun. 20, 2008, now abandoned.

(51) Int. Cl.
*G01N 21/84* (2006.01)
*G01N 33/28* (2006.01)
*G01N 21/64* (2006.01)

(52) U.S. Cl.
CPC ........... *G01N 21/84* (2013.01); *G01N 21/64* (2013.01); *G01N 21/643* (2013.01);
(Continued)

(58) Field of Classification Search
CPC ...... G01N 21/64; G01N 21/643; G01N 21/84; G01N 2201/061; G01N 33/2852; G01N 33/2882
(Continued)

(56) References Cited

U.S. PATENT DOCUMENTS 3,413,227 A 11/1968 Howard et al.
4,406,811 A * 9/1983 Christensen ............ C23F 11/10
106/14.12
(Continued)

FOREIGN PATENT DOCUMENTS

EP 0703451 A2 3/1996
WO WO 2009/155524 A1 12/2009

OTHER PUBLICATIONS

International Fuel Quality Center, "Setting a Quality Standard for Fuel Ethanol", 2004, International Fuel Quality Center, Hart Downstream Energy Services, pp. 1-56 (Year: 2004).*
(Continued)

*Primary Examiner* — Latosha Hines
(74) *Attorney, Agent, or Firm* — Leydig, Voit & Mayer, Ltd.

(57) ABSTRACT

Disclosed is a method of monitoring and optimizing the concentration of an additive composition in a fuel ethanol. The method includes adding a known amount of the additive composition to the fuel ethanol to create a treated fuel ethanol. A measured fluorescent signal provides information for determining the concentration of the additive composition in the fuel ethanol. A component in the additive composition is capable of providing the fluorescent signal or capable of being chemically derivatized to provide a fluorescent signal or a colorimetric signal. Based upon the measured fluorescent signal or colorimetric signal, the concentration of the additive composition in the fuel ethanol may be adjusted.

19 Claims, 2 Drawing Sheets

Corrosion Inhibitor A

Corrosion Inhibitor B

*Artifact due to diffraction gratings

(52) U.S. Cl.
CPC ..... *G01N 33/2852* (2013.01); *G01N 33/2882* (2013.01); *G01N 2201/061* (2013.01)

(58) Field of Classification Search
USPC .............................................. 250/206, 459.1
See application file for complete search history.

(56) References Cited

U.S. PATENT DOCUMENTS

| | | | |
|---|---|---|---|
| 4,426,208 A * | 1/1984 | Perilstein | C10L 1/18 |
| | | | 252/396 |
| 4,783,314 A * | 11/1988 | Hoots | G01F 1/704 |
| | | | 210/696 |
| 4,964,468 A | 10/1990 | Adams et al. | |
| 4,992,380 A | 2/1991 | Moriarty et al. | |
| 4,994,197 A | 2/1991 | Blain et al. | |
| 5,009,799 A | 4/1991 | Syrinek et al. | |
| 5,171,450 A | 12/1992 | Hoots | |
| 5,225,679 A * | 7/1993 | Clarke | G01N 33/2829 |
| | | | 250/339.12 |
| 5,278,074 A | 1/1994 | Rao et al. | |
| 5,358,873 A * | 10/1994 | Nowak | C10L 1/003 |
| | | | 436/178 |
| 5,702,684 A * | 12/1997 | McCoy | A01N 61/00 |
| | | | 210/745 |
| 5,843,783 A | 12/1998 | Rutledge et al. | |
| 6,107,531 A | 8/2000 | Colle et al. | |
| 6,255,118 B1 | 7/2001 | Alfano et al. | |
| 6,472,219 B1 | 10/2002 | Nieuwenhuis et al. | |
| 6,866,797 B1 | 3/2005 | Martin et al. | |
| 6,966,213 B2 | 11/2005 | Hoots et al. | |
| 6,984,340 B1 | 1/2006 | Brady et al. | |
| 7,057,050 B2 | 6/2006 | Meyer | |
| 7,909,101 B2 | 3/2011 | Conrad | |
| 7,951,754 B2 | 5/2011 | Tiwari et al. | |
| 7,989,403 B2 | 8/2011 | Acosta et al. | |
| 8,105,987 B2 | 1/2012 | Acosta et al. | |
| 8,105,988 B2 | 1/2012 | Acosta et al. | |
| 8,288,323 B2 | 10/2012 | Acosta et al. | |
| 8,329,620 B2 | 12/2012 | Acosta | |
| 8,334,240 B2 | 12/2012 | Acosta | |
| 8,551,925 B2 | 10/2013 | Nguyen et al. | |
| 8,585,930 B2 | 11/2013 | Tiwari | |
| 8,618,025 B2 | 12/2013 | Webber | |
| 8,618,027 B2 | 12/2013 | Meyer et al. | |
| 8,911,615 B2 | 12/2014 | Raney et al. | |
| 8,921,478 B2 | 12/2014 | Conrad et al. | |
| 2001/0029701 A1 | 10/2001 | Ahern et al. | |
| 2003/0006385 A1 | 1/2003 | Banks | |
| 2004/0157334 A1 | 8/2004 | Barashkov et al. | |
| 2005/0008532 A1 | 1/2005 | Jenkins et al. | |
| 2005/0025660 A1 | 2/2005 | Hoots et al. | |
| 2006/0214112 A1 | 9/2006 | Resch-Genger et al. | |
| 2008/0168708 A1 * | 7/2008 | Cunningham | C10L 1/023 |
| | | | 44/341 |
| 2009/0260454 A1 * | 10/2009 | Young | C23F 11/10 |
| | | | 73/861.13 |
| 2009/0319195 A1 | 12/2009 | Hoots et al. | |
| 2010/0099807 A1 | 4/2010 | Carlise et al. | |
| 2010/0099814 A1 | 4/2010 | Conrad et al. | |
| 2015/0034319 A1 | 2/2015 | Taylor | |

OTHER PUBLICATIONS

Schnegg et al., "Sonde for Downhole Measurement of Water Turbidity and Dye Tracer Concentration," in *Articles of Geomagnetism Group*, University of Neuchâtel, Swets & Zeitlinger, Lisse, The Netherlands, 2001, pp. 795-798.

International Fuel Quality Center, "Setting a Quality Standard for Fuel Ethanol," 2004, International Fuel Quality Center, Hart Downstream Energy Services, pp. 1-56.

Durst et al., "Phenacyl Esters of Fatty Acids Via Crown Ether Catalysts for Enhanced Ultraviolet Detection in Liquid Chromatography," 1975, *Analytical Chemistry*, 47(11): 1797-1801.

Erwin, "Symposium on Processing and Product Selectivity of Synthetic Fuels," American Chemical Society, Aug. 1992, pp. 1915-1923.

Gieleciak et al., "Detailed hydrocarbon analysis of FACE diesel fuels using comprehensive two-dimensional gas chromatography," Technical Report of Natural Resource Canada, Report CDEV-2013-2065-RT, Oct. 2013, 95 pp.

Thomas et al., "Analysis of Commercial Diesel Fuels by Preparative High Performance Liquid Chromatography and Gas Chromatography-Mass Spectrometry," *ACS Fuels Volumes Fall (Chicago)*, 1985, 30(4), pp. 76-84.

Wilde et al., "Techniques of Water-Resources Investigations of the United States Geological Survey, Book 9," U.S. Geological Survey, 1998-, pp. 18-28.

* cited by examiner

# METHOD OF MONITORING AND OPTIMIZING ADDITIVE CONCENTRATION IN FUEL ETHANOL

CROSS-REFERENCE TO RELATED APPLICATION

This application is a continuation of pending U.S. patent application Ser. No. 12/143,400, which was filed Jun. 20, 2008, the disclosure of which is incorporated herein by reference in its entirety.

TECHNICAL FIELD

This invention relates generally to methods of monitoring and/or controlling additive composition dosages in fuel ethanol. More specifically, the invention relates to monitoring and optimizing dosages of additive compositions including corrosion inhibitors, combinations of different corrosion inhibitors, denaturants, and mixtures of corrosion inhibitor(s) and denaturants in fuel ethanol. The invention has particular relevance to monitoring such dosages using fluorescence signals from one or more components in the additive composition.

BACKGROUND

Fuel ethanol production in the U.S. increased by about 440% during the period from 1996 to 2007 (from 1.1 to 6.5 billion gallons per year) and world ethanol production reached about 13.1 billion gallons per year in 2007. Fuel ethanol plants under construction/expansion are expected to double current U.S. production capacity, and legislation has been passed that could increase fuel ethanol demand by more than 600% by 2022.

Two most commonly used types of additives in fuel ethanol include denaturants and corrosion inhibitors, the use of which is growing concomitantly with the growth in fuel ethanol production. Inaccurate dosing of such additives can create a multitude of problems, including noncompliance with ASTM D-4806. For example, underdosing of corrosion inhibitor can lead to corrosion problems, whereas overdosing wastes chemicals and causes higher production costs. High dosages of some fuel ethanol corrosion inhibitors have also been linked to increases in intake valve deposits, which can cause substantial engine operational issues.

Inaccurate dosing of denaturant causes significant government regulatory and legal problems. Releasing inaccurately dosed batches of fuel ethanol would likewise violate ASTM D-4806. Both underdosing and overdosing of denaturant leads to out-of-specification results that in turn lead to higher production/shipping costs and delays due to rework of batches.

The maximum specification range currently allowed in the U.S. for denaturant is typically about 1.96 to 4.76% by volume. Due to the cost differential between ethanol and denaturant, it is valuable for a fuel ethanol plant to have the ability to be as close as possible to the upper or lower edge of denaturant dosage specification range. When ethanol costs exceed denaturant costs, for instance, it is desirable for the fuel ethanol plant to be at the high dosage edge of denaturant specification range to keep production costs to a minimum. On the other hand, when denaturant costs more than ethanol, it is desirable for the fuel ethanol plant to be at the low dosage edge of denaturant specification range.

To operate near either edge of the additive dosage specification range requires highly accurate and precise measuring/dosing of additive concentration. Presently, fuel ethanol plants tend to dose additives via splash blending and/or based on how "long" a chemical feed pump is "on" with a "constant flowrate assumed" or sometimes based on flowmeters or depth gauges. Even when such flowmeters are regularly and properly calibrated, proper dosage rates are not always achieved. Very rarely (if ever) is dosage of ethanol additives directly measured. Also, batch-to-batch variations and the complex chemical nature of ethanol additives increase difficulty of precisely and accurately measuring additive dosages with currently used methods.

There thus exists an ongoing need to develop methods of accurately and efficiently monitoring and controlling additive concentrations in fuel ethanol production plants. Such methods would allow the fuel ethanol producer to easily minimize costs of production by adjusting formulations based upon raw material costs and to maximize the quality and value of the fuel ethanol product.

SUMMARY

This invention accordingly includes methods of monitoring and optimizing dosage of one or more fuel ethanol additives by measuring a fluorescent signal. Such measurements are taken, for example, from one or more components of an additive composition, a derivative of a component in the additive, and/or from an inert tracer used in conjunction with or as part of the additive to provide an indication of dosage concentration. It is contemplated that the described method may be applied to any additive for fuel ethanol. In a preferred embodiment, the method is applied to measuring and controlling dosages of denaturants and/or corrosion inhibitors. Such monitoring and control may be directed to additives present in or added to the fuel ethanol. Depending upon whether a denaturant or corrosion inhibitor is the traced additive (and the particular chemistry used), the chosen method of measuring the fluorescent signal may be different. Alternative methods of measuring additive concentrations include, for example, an additive having an intrinsically fluorescent component, adding an inert fluorescent tracer (monitoring/control on-line or by grab sample), or adding a fluorometric or colorimetric reagent that reacts with one of the components of the additive formulation (grab sample). Certain limitations and extensions of these alternatives are explained in more detail below.

It is an advantage of the invention to provide an easy, accurate, and precise method to measure additive dosages in fuel ethanol and to definitively adjust the dosage setpoint as needed.

It is another advantage of the invention to provide methods of controlling additive dosages at fuel ethanol manufacturing plants thereby significantly reducing operating costs by preventing inaccurate dosing of treatment chemicals.

An additional advantage of the invention is to enable fuel ethanol producers to include certificates of analysis with respect to additive dosage for each fuel ethanol shipment.

It is also an advantage of the invention to provide accurate measurements of additive dosages in fuel ethanol for compliance with government regulations.

A further advantage of the invention is to provide a versatile method of monitoring and controlling additive dosages in fuel ethanol that could be used in both a grab sample analysis scheme and/or adapted to online dosage control with datalogging capabilities.

Another advantage of the invention is to provide a method of compensating for changes in fuel ethanol system characteristics by adjusting additive dosage.

Yet another advantage of the invention is to provide methods of controlling additive dosages at fuel ethanol manufacturing plants to eliminate the possibility of out-of-specification product batches and prevent costly reworking of batches to achieve specification and/or government compliance.

Additional features and advantages are described herein, and will be apparent from, the following Detailed Description, Examples, and Figures.

DETAILED DESCRIPTION

Figure 1:
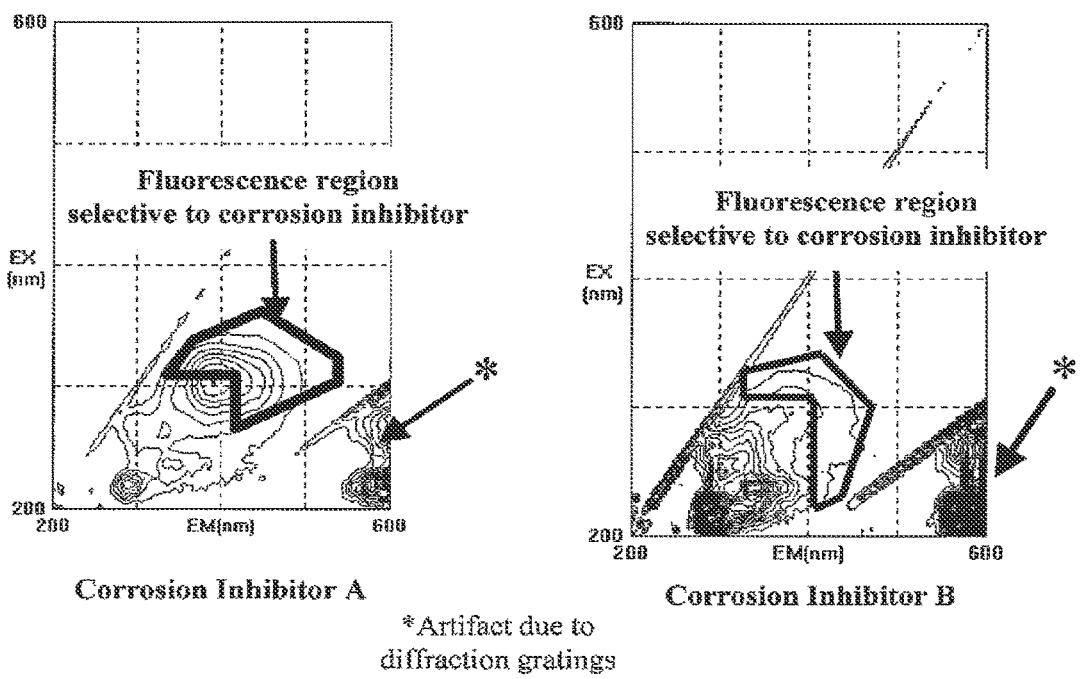
FIG. 1 shows the ability to measure intrinsic fluorescence of components in two different commercially available fuel ethanol corrosion inhibitors, illustrated as contour fluorescence spectra.

In preferred embodiments, the invention includes methods of monitoring, regulating, and/or optimizing the concentration of an additive composition in a fuel ethanol using a fluorescent signal generated from a component in the additive composition. The disclosed method of this invention is suitable for all manner of fuel ethanol production and is compatible with essentially all grades of fuel ethanol mixtures. The method is particularly well suited for use in conjunction with a variety of fuel ethanol additives. Application of the method begins in the production process where additives including denaturants and/or corrosion inhibitors are typically added, and may also be implemented at any stage of the packaging and shipping process. The described method is equally applicable to various sampling techniques including grab samples, sidestream and inline measurements, and measurements taken from a bulk container or vessel.

It should be appreciated that the method, in certain embodiments, may be combined with other utilities known in the ethanol industry. Representative utilities include sensors for measuring alcohol content in, for example, gasoline; sensors for determining fuel composition; individual alcohol concentration sensors (e.g., methanol, ethanol); alcohol/gasoline ratio sensors; dissolved or particulate contaminant sensors; other sensors based upon resistance, capacitance, spectroscopic absorbance, colorimetric measurements, and fluorescence; and mathematical tools for analyzing sensor/controller results (e.g., multivariate analysis, chemometrics, on/off dosage control, PID dosage control, the like, and combinations thereof).

In addition to solvents, stabilizers, and other components, the additive composition typically has a corrosion inhibitor, denaturant, or a mixture of both. The additive may also be a neat product or a mixture of two or more additives. It should be appreciated that the additive composition may include any number of compounds or components. Although such additives are most commonly a corrosion inhibitor or denaturant (or combination), as explained above, the described method is equally suited to any additive composition in used in fuel ethanol. Executing the method involves adding a known amount of the additive composition to the fuel ethanol to create a treated fuel ethanol. The added amount is calculated to provide an optimum concentration range for the additive composition in the treated fuel ethanol.

One limitation is that the intrinsic fluorescence of different batches of denaturants has significantly variable fluorescence intensities and peak shapes. Though technically feasible, it is not a preferred method of the invention to use the inherent or intrinsic fluorescence of denaturant additives for monitoring and optimizing the dosage of fuel ethanol additives unless the denaturant has a consistent chemical composition. The intrinsic fluorescence of corrosion inhibitor formulations, however, is acceptable when properly implemented and is a preferred embodiment of the invention. Methods utilizing fluorescent tracers have equal efficacy in all types of additive formulations.

In an embodiment, the additive composition includes a corrosion inhibitor. It is contemplated that the described method is operable with any corrosion inhibitor used for fuel ethanol. For example, a corrosion inhibitors containing compounds such as organic acid anhydrides; monomer, dimer, and/or trimer organic fatty acid mixtures; and tertiary organic amines may be used. Corrosion inhibitors also typically include a mixture of one or more of the following: organic (cyclohexyl-containing) amine; monomer, dimer, and/or trimer organic fatty acids including synthetics; organic acid anhydride; and organic solvents such as alcohol, xylenes, or other hydrocarbon-based solvent. The optimum concentration range for corrosion inhibitor products is typically in the ppm range (see Examples), although this range may be above or below the optimum target dosage for certain applications. It should be appreciated that the described method is applicable for use with any corrosion inhibiting composition.

In another embodiment, the additive composition includes a denaturant. Typical denaturants include condensates from natural gas condensate, which may include gasoline, methanol, straight-chain hydrocarbons, naphthenes, aromatics, and others. It should be appreciated that any denaturant known in the art may be used with the method of the invention.

The additive composition includes at least one component that is either inherently capable of providing a fluorescent signal or capable of being chemically derivatized or functionalized to provide a fluorescent signal. Fluorescence behavior has been found to be markedly and unexpectedly different in ethanol than in aqueous, ethanol-free solutions or low polarity hydrocarbon-containing solutions. Intensive testing and experimentation was required to ascertain effective fluorescing molecules and moieties in ethanol-containing systems (see Example 2).

In one embodiment, a component that is normally a part of a conventional additive composition is inherently fluorescent. Such an additive is, for example, a corrosion inhibitor composition having a solvent containing an aromatic hydrocarbon. Xylene, other aromatic hydrocarbons, and functionalized aromatic hydrocarbons are inherently fluorescent and its fluorescent signal may be used as an analytical signal to determine the concentration of the additive composition in a treated fuel ethanol. FIG. 1 illustrates two different commercially used corrosion inhibitors that exhibit such inherent fluorescence and fluorescence excitation/emission wavelength combinations where the intrinsic fluorescence corrosion inhibitor is different from the intrinsic fluorescence of denaturant, contaminants, etc.

Alternatively, a component that does not inherently provide an analytical signal but that is normally part of the additive composition can be chosen for modification, such as in a grab sample or sidestream taken from the system. This component is derivatized or functionalized with a moiety that imparts that ability to provide a fluorescent signal or a colorimetric signal. A compound in a corrosion inhibitor composition may chemically be derivatized with a fluorescent moiety or reacted to provide a colorimetric signal. According to an embodiment, a component of the corrosion inhibitor (e.g., tertiary organic amine) may be reacted with aromatic carbonyl chloride (Ar—COCl) in a grab sample analysis method to measure the amount of corrosion inhibitor present in the fuel ethanol at any given point (See Coppex, L., Derivatives for HPLC analysis, November 1999 to February 2000). Derivatization agents can be used to react with any component of the fuel ethanol corrosion inhibitor to utilize a fluorescent analysis technique. For example, 4-bromomethyl-7-methoxy-coumarin can react with carboxylic acids to form a fluorescent derivative (See W. Dunges, in "Analytical Chemistry," vol. 49, p. 442, 1977). In another example, carboxylic acids (e.g., dimer fatty acids) in a corrosion inhibitor may be reacted to produce a colorimetric signal. A representative carboxylic acid reagent is p-bromophenacyl bromide (PBPB). (See Durst et al., in "Analytical Chemistry," vol. 47, p. 1747, 1975).

In a preferred embodiment, an inert fluorescent tracer is included in the additive composition. A known proportion of the fluorescent tracer is added either simultaneously or sequentially with the additive composition. Preferably, the inert fluorescent tracer is added first to the additive composition and the tracer-containing additive is then combined with the fuel ethanol or combined with another additive (e.g., traced corrosion inhibitor formulation combined with denaturant), which combination is added to the fuel ethanol.

Effective inert fluorescent tracers include those substances that are chemically non-reactive with other components in the fuel ethanol and that do not significantly degrade with time. Such tracers should also be completely (or essentially completely) soluble in the additive formulation, mixtures of additives, and mixtures of additive(s) and fuel ethanol at all relevant levels of concentration and preferably the fluorescence intensity should be substantially proportional to its concentration and not significantly quenched or otherwise diminished by the fuel ethanol or other components in the fuel ethanol. Furthermore, the inert fluorescent tracer should not be appreciably or significantly affected by any other chemistry in fuel ethanol. The statement, "not appreciably or significantly affected," means that an inert fluorescent compound generally has no more than about a 10% change in its fluorescent signal, under conditions normally encountered in fuel ethanol.

Desired characteristics for an inert fluorescent tracer preferably include: fluorescence excitation/emission wavelengths that do not have significant overlap with light absorbing substances in the fuel ethanol, other additives, contaminants, etc.; high solubility in an additive (and combinations of additives) and additive(s) combination with fuel ethanol; excellent chemical stability; suitable fluorescence properties at manageable wavelengths (e.g., other additives in the fuel ethanol should not interfere with the fluorescence properties at those wavelengths) and excitation/emission wavelengths that are separate from other fluorescent components in the fuel ethanol and additive mixtures to prevent interference; chemical composition typically containing only C, H, N, O, and/or S (where S content of fuel ethanol<15 ppm of total composition, and avoiding "S" if possible); and avoiding negative impacts on fuel properties.

Furthermore, ideal inert fluorescent tracers would: not be significantly impacted by surrounding temperature or pressure; presence of water or other solvents; have acceptably low light absorbance; lack metal ions, phosphorous, and halides; not be impacted by changes in the composition of other additives or contaminants (e.g., butanol); should not adversely alter performance of additives, such as pH buffering ability of corrosion inhibitor, sufficiently burned when fuel ethanol mixtures are used in internal combustion engines; and not cause deposits, fouling, corrosion, etc. in downstream applications.

Representative inert fluorescent tracers that do not have metal ion/halide counterions or halide functional groups include fluorescein or fluorescein derivatives; rhodamine or rhodamine derivatives; naphthalene sulfonic acids (mono-, di-, tri-, etc.); pyrene sulfonic acids (mono-, di-, tri-, tetra-, etc.); stilbene derivatives containing sulfonic acids (including optical brighteners); biphenyl sulfonic acids; phenylalanine; tryptophan; tyrosine; vitamin B2 (riboflavin); vitamin B6 (pyridoxin); vitamin E (α-tocopherols); ethoxyquin; caffeine; vanillin; naphthalene sulfonic acid formaldehyde condensation polymers; phenyl sulfonic acid formaldehyde condensates; lignin sulfonic acids; polycyclic aromatic hydrocarbons; aromatic (poly)cyclic hydrocarbons containing amine, phenol, sulfonic acid, carboxylic acid functionalities in any combination; (poly)heterocyclic aromatic hydrocarbons having N, O, or S; a polymer containing at least one of the following moieties: naphthalene sulfonic acids, pyrene sulfonic acids, biphenyl sulfonic acids, or stilbene sulfonic acids. Additional examples of such inert fluorescent tracers may be found in U.S. Pat. No. 6,966,213 B2, entitled "Rapid Method for Detecting Leaks of Hydraulic Fluids in Production Plants" and U.S. Pat. No. 7,169,236 B2, entitled "Method of Monitoring Membrane Cleaning Process." These inert fluorescent tracers are either commercially available under the tradename TRASAR® from Nalco Company® (Naperville, Ill.) or may be synthesized using techniques known to persons of ordinary skill in the art of organic chemistry.

It should be appreciated that the process of selecting an inert fluorescent tracer, such as a polyaromatic hydrocarbon ("PAH"), requires substantial experimentation to determine those PAHs suitable for use as an inert fluorescent tracer. It was unexpectedly found that some PAHs (containing solubilizing groups, such as sulfonates (e.g., 1,3,6,8-pyrene tetrasulfonic acid)) that are effective as fluorescent tracers in aqueous systems, the corresponding PAH (e.g., pyrene) is unfavorable in fuel ethanol formulations due to weak or no fluorescence or encountered high background fluorescence from other PAHs such as naphthalene, chrysene, and certain other 2 to 4 aromatic ring PAHs. Anthracene and perylene, for example, showed strong fluorescence in fuel ethanol systems, 3 and 5 aromatic ring PAHs, respectively.

Figure 2:
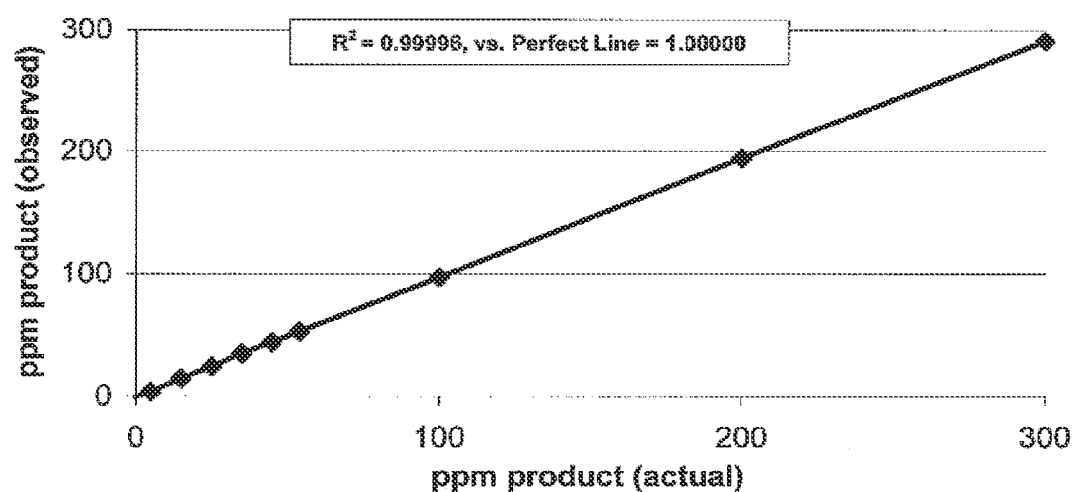
FIG. 2 illustrates the linearity and predictability of fluorescence in a preferred embodiment where an inert fluorescent tracer was added in a corrosion inhibitor composition added to fuel ethanol, as explained in Example 8.

Regardless of which of the described fluorescent methods is used, a working curve for the particular fluorophore chosen, such as that shown in FIG. 2, should be developed. Similar curves can be readily created for any desired fluorophore when the fluorescence analysis conditions (for example, excitation and emission wavelength) are defined. The present fluorometric method requires the selection of an excitation wavelength to activate the fluorescence process and an emission wavelength at which fluorescence intensity is to be measured, which preferably is substantially free of interference from other species present in the fuel ethanol being monitored. Undesirable interference may be encountered when one or more other species have significant fluorescence emission or light absorbance at about the excitation/emission wavelengths selected for monitoring the chosen fluorophore. The excitation wavelength is chosen to also prevent photodegradation from occurring.

The background fluorescent signal may be measured in the treated fuel ethanol at any point subsequent to adding the additive composition. "Treated fuel ethanol" refers to fuel ethanol including the additive composition as herein described.

In alternative embodiments, the fluorescent signal is acquired at one, two, or more points.

In a preferred embodiment, the fluorescent signal is acquired online, either continuously or intermittently. Such online measurements may be analyzed in real-time or with a user-defined or other delay. For example, online measurements may take place by using a side-stream, inline, or other suitable flow-through device.

In another embodiment, a sample of treated fuel ethanol is removed, either automatically or manually, and the fluorescent signal is acquired from the removed sample.

Based upon the fluorescent signal, the total or component concentration of the additive composition may be determined. Three possible scenarios exist for the outcome of this determination. The first is that the concentration of the additive composition is within the optimum concentration range. In this instance, no further action would be taken. In the event the determined concentration of the additive composition is higher than the optimum concentration range, the treated fuel ethanol would optionally be diluted with a known additional volume of fuel ethanol. The additional volume would be calculated to bring the concentration of the additive composition into the optimum concentration range. If the determined concentration of the additive composition is below the optimum concentration range, an additional amount of the additive composition would optionally be introduced into the treated fuel ethanol in an amount calculated to bring the concentration of the additive composition into the optimum concentration range. The method of the invention may optionally be repeated (e.g., in an iterative fashion) until the determined concentration of the additive composition is within the optimum concentration range (or another chosen concentration range, such as a user-selected concentration range).

Fuel ethanol (usually approximately E95) is typically mixed with gasoline to form ethanol-containing gasolines, such as E10 and E85. For example, an E10 formulation generally includes about 9.5 to 9.8% vol/vol ethanol, about 0.2% to 0.5% vol/vol denaturant, and about 90% vol/vol gasoline. The described method is equally applicable in such fuel ethanol compositions, including determining the total ethanol content in an alternative embodiment.

A manual operator or an electronic device having components such as a processor, memory device, digital storage medium, cathode ray tube, liquid crystal display, plasma display, touch screen, or other monitor, and/or other components may be used to execute all or parts of the described method. In certain instances, the controller may be operable for integration with one or more application-specific integrated circuits, programs, computer-executable instructions, or algorithms, one or more hard-wired devices, wireless devices, and/or one or more mechanical devices. Some or all of the controller system functions may be at a central location, such as a network server, for communication over a local area network, wide area network, wireless network, Internet connection, microwave link, infrared link, and the like. In addition, other components such as a signal conditioner or system monitor may be included to facilitate signal-processing algorithms. It is also contemplated that any needed sensors, couplers, connectors, or other data measuring/transmitting/communicating equipment may be used to capture and transmit data.

The foregoing description may be better understood by reference to the following examples, which are intended for illustrative purposes and are not intended to limit the scope of the invention.

Example 1

To demonstrate corrosion inhibitor concentration variability, a series of 40 samples were collected from seven different fuel ethanol manufacturing plants (designated as "Source" in Table 1), where corrosion inhibitor was being dosed by manual addition, such as splash addition or other indirectly measured methods. The dosages of corrosion inhibitor were measured by fluorescence measurement of the inherent fluorescence of corrosion inhibitor formulation. Table 1 summarizes the average, maximum and minimum dosages, and variability in the corrosion inhibitor dosages measured due to all sources of variability. The recommended "target dosage" of corrosion inhibitor is often 72 ppm (weight/weight) or 20 pounds per thousand barrels of ethanol ("PTBE") for several commercially used products listed in Renewal Fuels Association list of corrosion inhibitor products. Table 2 illustrates industry recommended treatment rates for several commercially available corrosion inhibitors, where 1 PTBE=3.59 ppm or 20 PTBE=72 ppm (see Renewable Fuels Association Memorandum, entitled "Corrosion Inhibitor in Fuel Ethanol, Industry Guidelines, Specifications, and Procedures," published Sep. 10, 2007). Each product is a trademark of the respective owner.

Dosage results in Table 1 are listed as ppm. The variability in dosage is given as ±3 SIGMA and as % deviation from average, which is based upon an assumption of a statistically normal distribution. The results from the 40 samples are that overall average dosage (51 ppm) is significantly below the recommended target dosage of 72 ppm. The average dosages in Table 1 are typically significantly below the recommended target dosage with many samples being much below (and some samples being significantly above) the recommended target dosage.

The variability +/−3 SIGMA or 99.7% probability that readings will occur in a range from "average+3 SIGMA" to "average−3 SIGMA" was unacceptably high in each case, indicating that dosage control was poor in the systems surveyed. The higher the +/−3 SIGMA value (expressed as % of "Avg ppm"), the more variable the readings are and the poorer the dosage control. These results demonstrate the significant industry need for more accurate corrosion inhibitor dosage control than currently exists.

TABLE 1

| Source | # of Samples | Max ppm | Min ppm | Avg ppm | Variability (in ppm) as ±3 SIGMA | % Variability (±3 SIGMA) relative to Avg |
|---|---|---|---|---|---|---|
| A | 4 | 29 | 20 | 24 | ±14 | ±58% |
| B | 7 | 55 | 4 | 23 | ±59 | ±256% |
| C | 14 | 82 | 27 | 52 | ±55 | ±106% |
| D | 3 | 176 | 53 | 94 | ±212 | ±225 |
| E | 2 | 100 | 84 | 92 | N/A | N/A |
| F | 3 | 150 | 45 | 89 | ±55 | ±62 |
| G | 1 | 30 | N/A | N/A | N/A | N/A |
| H | 6 | 19 | 89 | 49 | ±77 | ±157% |
| Overall | 40 | 176 | 4 | 51 | ±106 | ±208 |

TABLE 2

| Additive | Dosage (PTBE) | Dosage (ppm) |
|---|---|---|
| Innospec Octel DCI-11 | 20 | 72 |
| Petrolite Tolad 3222 | 20 | 72 |
| Petrolite Tolad 3224 | 13 | 47 |
| Nalco 5403 | 30 | 108 |
| ENDCOR FE-9730 (formerly Betz CAN 13) | 20 | 72 |
| MidContinental MCC5011E | 20 | 72 |
| MidContinental MCC5011EW | 27 | 97 |
| US Water CorrPro 654 | 13 | 47 |
| Nalco EC 5624A | 15 | 54 |
| Afton Chemical Bio Tec 9880 | 10 | 36 |
| Lubrizol LZ 541 | 16 | 57 |
| US Water CorrPro 656 | 13 | 47 |

An independent method based on a tertiary amine component of the corrosion inhibitor formulation also confirmed a high level of product dosage variability with a significant number of samples much higher or much lower than the recommended target dosage rate.

Examples 2 to 5

Examples 2 to 5 illustrate the differences between current methods of adjusting additive dosages; direct manual measurement of traced corrosion inhibitor, either with or without providing a measurement for added denaturant (by tracer fluorescence); and automatic control of corrosion inhibitor dosage, either with or without providing a measurement for added denaturant, based on fluorescence measurements of traced corrosion inhibitor being added to fuel ethanol. In each of these examples, it can be seen that fluorescence of tracer added to corrosion inhibitor product to measure corrosion inhibitor dosage could significantly improve accuracy and reduce variability. Manual adjustment of product dosage after measuring of corrosion inhibitor concentration would provide for improved additive dosage accuracy and reduced variability in final treated fuel ethanol. Online monitoring/control of corrosion inhibitor dosage would result in further improved accuracy and reduced variability in concentration levels. The predicted variability is shown as ±3 SIGMA and based on assumption that a statistically normal distribution would occur.

Example 2

To illustrate corrosion inhibitor dosage monitoring and/or control by inherent fluorescence of a component in an additive formulation, a corrosion inhibitor may initially be added by the plant to series of batches of fuel ethanol using a "splash addition" method (standard industry practice). The estimated volume of corrosion inhibitor to be added is typically based on the estimated volume of fuel ethanol in the storage tank. The theoretical results in Table 3 shows dosage of corrosion inhibitor during three phases of dosage monitoring and/or control. Batch numbers 1 to 5 illustrate dosage prior to any changes in corrosion inhibitor dosing procedure (i.e., manual addition with no measurement during addition of corrosion inhibitor); 6 to 10 show improved results with direct measurement of corrosion inhibitor (by inherent fluorescence) and manual addition/adjustment of corrosion inhibitor based on measurement of corrosion inhibitor; and 11 to 15 exemplify further improvement in results (average closer to target dosage and lower±SIGMA value) due to automatic measurement and dosage control of corrosion inhibitor dosage based on inherent fluorescence measurements of the corrosion inhibitor being added to fuel ethanol. The target dosage of corrosion inhibitor is 72 ppm in fuel ethanol mixture for this Example. Predicted variability is shown as ±3 SIGMA and based on assumption that a statistically normal distribution occurs.

TABLE 3

| Manual addition w/out measurement during addition | | Manual addition/adjustment with measurement during addition | | Automatic measurement and dosage control | |
|---|---|---|---|---|---|
| Batch # | Dosage (ppm) | Batch # | Dosage (ppm) | Batch # | Dosage (ppm) |
| 1 | 50 | 6 | 77 | 11 | 74 |
| 2 | 32 | 7 | 79 | 12 | 75 |
| 3 | 100 | 8 | 76 | 13 | 72 |
| 4 | 71 | 9 | 71 | 14 | 74 |
| 5 | 25 | 10 | 67 | 15 | 70 |
| Avg. ± 3 SIGMA | 56 ± 92 | Avg. ± 3 SIGMA | 74 ± 15 | Avg. ± 3 SIGMA | 73 ± 6 |

Example 3

To show corrosion inhibitor dosage monitoring and/or control by addition of a fluorescent tracer to an additive formulation, a small known amount of fluorescent tracer could be added into corrosion inhibitor formulation during its manufacture. Traced corrosion inhibitor may initially be added by the plant to series of batches of fuel ethanol using a "splash addition" method. Estimated volume of corrosion inhibitor to be added is typically based on estimated volume of fuel ethanol in storage tank. Results in Table 4 show theoretical dosage of traced corrosion inhibitor during three phases of dosage monitoring and/or control. Batch numbers 1 to 5 show results prior to any changes in corrosion inhibitor dosing procedure using a manual addition method and no measurement; 6 to 10 illustrate improved dosage using direct measurement of traced corrosion inhibitor (by tracer fluorescence) and manual addition/adjustment of corrosion inhibitor, and 11 to 15 exemplify further improvement in results due to automatic control of corrosion inhibitor dosage based on fluorescence measurements of traced corrosion inhibitor being added to fuel ethanol. Target dosage of traced corrosion inhibitor is 72 ppm in fuel ethanol mixture in this Example.

TABLE 4

| Manual addition w/out measurement during addition | | Manual addition/adjustment with measurement during addition | | Automatic measurement and dosage control | |
|---|---|---|---|---|---|
| Batch # | Dosage (ppm) | Batch # | Dosage (ppm) | Batch # | Dosage (ppm) |
| 1 | 25 | 6 | 67 | 11 | 73 |
| 2 | 32 | 7 | 74 | 12 | 71 |
| 3 | 85 | 8 | 71 | 13 | 70 |
| 4 | 54 | 9 | 73 | 14 | 72 |
| 5 | 104 | 10 | 68 | 15 | 73 |
| Avg. ± 3 SIGMA | 60 ± 102 | Avg. ± 3 SIGMA | 71 ± 9 | Avg. ± 3 SIGMA | 72 ± 4 |

The use of fluorescent traced corrosion inhibitor also allows a ready means to identify that the correct additive was mixed with the fuel ethanol. If the fluorescence signal of the traced corrosion inhibitor is absent or at significantly reduced level in the treated fuel ethanol, that measurement demonstrates: (i) an incorrect corrosion inhibitor product was used; (ii) that the treated fuel ethanol was diluted with an untraced corrosion inhibitor, (iii) that the batch of treated fuel ethanol was mixed with another batch of fuel ethanol that was treated with an untraced or incorrect corrosion inhibitor, or (iv) that batches of fuel ethanol that were correctly and incorrectly treated were mixed.

Example 4

Fluorescent tracer may be added to corrosion inhibitor and then the traced corrosion inhibitor may be mixed into denaturant at a prescribed dosage to provide monitoring and/or control of denaturant and traced corrosion inhibitor dosage. Under current legal standards, denaturant can typically be added from about 1.96% up to about 4.76% volume/volume (or about 1.63% to about 3.98% weight/weight) into fuel ethanol, depending on the locality of fuel ethanol manufacture. If the target dosage for corrosion inhibitor was 72 ppm (or 0.072% weight/weight) and denaturant was 2.20% volume/volume (1.83% weight/weight), the traced corrosion inhibitor may be added to denaturant in a ratio of 1 part traced corrosion inhibitor to 25.4 parts (by weight/weight) of denaturant. The mixture of denaturant and traced corrosion inhibitor may then be added to the fuel ethanol and the dosages of denaturant and corrosion inhibitor can both be monitored and/or controlled based on the fluorescent tracer signal.

Results in Table 5A to 5C show theoretical dosage of traced corrosion inhibitor and denaturant during three phases of dosage monitoring and/or control: (A) prior to any changes in corrosion inhibitor and denaturant dosing procedure with manual dosage control, (B) with direct measurement of traced corrosion inhibitor and denaturant (by tracer fluorescence) and with manual corrosion inhibitor addition, and (C) automatic control of corrosion inhibitor and denaturant dosages based on fluorescence measurements of the traced corrosion inhibitor+denaturant mixture being added to fuel ethanol. Target dosage of corrosion inhibitor is typically 72 ppm and 2.20% volume/volume (or 1.84% weight/weight) denaturant to produce treated fuel ethanol.

TABLE 5A

Manual Addition with Measurement

| Batch # | Corr. Inh. (ppm) | Denat. (% vol/vol) |
|---|---|---|
| 1 | 61 | 1.86 |
| 2 | 92 | 2.81 |
| 3 | 105 | 3.21 |
| 4 | 70 | 2.14 |
| 5 | 127 | 3.88 |
| Avg. ± 3 SIGMA | 91 ± 80 | 2.78 ± 2.44 |

TABLE 5B

Traced Additive with Manual Addition/Adjustment During Measurement

| Batch # | Corr. Inh. (ppm) | Denat. (% vol/vol) |
|---|---|---|
| 6 | 77 | 2.35 |
| 7 | 79 | 2.41 |
| 8 | 75 | 2.29 |
| 9 | 71 | 2.17 |
| 10 | 70 | 2.14 |
| Avg. ± 3 SIGMA | 74 ± 12 | 2.27 ± 0.35 |

TABLE 5C

Automated Measurement and Dosage Control

| Batch # | Corr. Inh. (ppm) | Denat. (% vol/vol) |
|---|---|---|
| 11 | 74 | 2.26 |
| 12 | 73 | 2.23 |
| 13 | 70 | 2.14 |
| 14 | 72 | 2.20 |
| 15 | 70 | 2.14 |
| Avg. ± 3 SIGMA | 72 ± 5 | 2.19 ± 0.16 |

The results above demonstrate that using fluorescence of traced corrosion inhibitor plus denaturant mixture to measure corrosion inhibitor and denaturant dosages can significantly improve accuracy and reduce variability in concentration of both additives. For example, it can be seen that Batch #1 in Table 5A has a denaturant vol % that is less than specification range of 1.96% to 4.76%, with a concomitantly low inhibitor dosage and overall high average dosage of denaturant and corrosion inhibitor and high variability in dosage of those two additions. That batch of treated ethanol would require additional denaturant plus traced fluorescent corrosion inhibitor mixture to meet specifications and regulatory/legal requirements.

Example 5

In order to measure and/or control higher dosages of denaturant, the target dosage for fluorescent traced corrosion inhibitor can be increased, the level of traced fluorescent corrosion inhibitor can be increased in its mixture with denaturant, the level of corrosion inhibitor can be adjusted. In this scenario, fluorescent tracer would be added to corrosion inhibitor and then the traced corrosion inhibitor mixed into denaturant at a prescribed dosage to provide monitoring and/or control of higher dosages of denaturant and traced corrosion inhibitor dosage. Current legal guidelines allow for a denaturant range from 1.96% up to 4.76% on a volume/volume basis (or 1.63% to 3.98% weight/weight) into fuel ethanol, depending on the locality of fuel ethanol manufacture. If the target dosage for corrosion inhibitor was 72 ppm (or 0.072% weight/weight) and denaturant was 4.50% volume/volume (3.74% weight/weight), then traced corrosion inhibitor would be added to denaturant in a ratio of 1 part traced corrosion inhibitor to 51.9 parts (by weight/weight) of denaturant. The mixture of denaturant and traced corrosion inhibitor would be added to the fuel ethanol and the dosages of denaturant and corrosion inhibitor would both be monitored and/or controlled based on the fluorescent tracer signal.

Results in Tables 6A to 6C show dosage of traced corrosion inhibitor added to denaturant during three phases of dosage monitoring and/or control of addition of that mixture: (A) prior to any changes in corrosion inhibitor and denaturant dosing procedure with manual addition of corrosion inhibitor, (B) with direct measurement of traced corrosion inhibitor and denaturant (by tracer fluorescence) and with manual addition of corrosion inhibitor, and (C) automatic control of corrosion inhibitor and denaturant dosages based on fluorescence measurements of the traced corrosion inhibitor plus denaturant mixture being added to fuel ethanol.

TABLE 6A

Manual Addition with Measurement

| Batch # | Corr. Inh. (ppm) | Denat. (% vol/vol) |
|---|---|---|
| 1 | 71 | 4.44 |
| 2 | 102 | 6.38 |
| 3 | 52 | 3.25 |
| 4 | 64 | 4.00 |
| 5 | 74 | 4.63 |
| Avg. ± 3 SIGMA | 73 ± 55 | 4.54 ± 3.47 |

TABLE 6B

Traced Additive with Manual Addition/Adjustment During Measurement

| Batch # | Corr. Inh. (ppm) | Denat. (% vol/vol) |
|---|---|---|
| 6 | 73 | 4.56 |
| 7 | 72 | 4.50 |
| 8 | 73 | 4.56 |
| 9 | 65 | 4.06 |
| 10 | 71 | 4.44 |
| Avg. ± 3 SIGMA | 71 ± 10 | 4.42 ± 0.63 |

TABLE 6C

Automatic Measurement and Dosage Control

| Batch # | Corr. Inh. (ppm) | Denat. (% vol/vol) |
|---|---|---|
| 11 | 73 | 4.56 |
| 12 | 70 | 4.38 |
| 13 | 72 | 4.50 |
| 14 | 73 | 4.56 |
| 15 | 74 | 4.63 |
| Avg. ± 3 SIGMA | 72 ± 5 | 4.53 ± 0.28 |

It can be seen that the dosage for Batch #2 of Table 6A was outside of the 1.96% to 4.76% (volume/volume) specification and legal limit range for denaturant in fuel ethanol, as well as having a high corrosion inhibitor dosage. That batch of treated ethanol would require dilution with an additional volume of untreated fuel ethanol to meet specifications and regulatory/legal requirements.

Example 6

A hand-held fluorometer calibrated for use with Rhodamine B base (CAS No. 509-34-2) inert fluorescent tracer was tested. The test was performed with Nalco EC 5624A containing 0.008 wt % Rhodamine B base, which yields 4.32 ppb Rhodamine B base when the corrosion inhibitor composition was dosed the recommended treatment rate of 54 ppm. A calculated amount of the traced corrosion inhibitor composition was added to a volume of fuel ethanol to give a final concentration of 54 ppm the corrosion inhibitor. Ten samples were independently tested to ascertain repeatability. Results presented in Table 7 below. The average determined concentration of the corrosion inhibitor was 53.6 ppm±0.8 ppm (at ±3 SIGMA), which translates to 4.29±0.06 ppb of Rhodamine B base.

TABLE 7

| Sample # | Corrosion Inhibitor Dosage (ppm) | Tracer (ppb) |
|---|---|---|
| 1 | 53.9 | 4.31 |
| 2 | 53.8 | 4.30 |
| 3 | 53.4 | 4.27 |
| 4 | 54.0 | 4.32 |
| 5 | 53.5 | 4.28 |
| 6 | 53.7 | 4.30 |
| 7 | 53.2 | 4.26 |
| 8 | 53.7 | 4.30 |
| 9 | 53.3 | 4.26 |
| 10 | 53.5 | 4.28 |
| Average ± 3 SIGMA | 53.6 ± 0.8 (target = 54) | 4.29 ± 0.06 (target = 4.32) |

Example 7

FIG. 2 illustrates the linearity and predictability of fluorescence where Rhodamine B base was used as the inert fluorescent tracer (about 0.006% wt/wt) in Corrosion Inhibitor B and added to fuel ethanol. The test was conducted with a range of the corrosion inhibitor concentration from 0 to 300 ppm. Excellent linearity of response was observed ($R^2$=0.999, where 1.00=perfect linearity). Excitation wavelength was 540 nm and emission wavelength was 560 nm.

Example 8

Table 8 below illustrates a nonexhaustive list various excitation and emission wavelength ranges that may be used in the method of the invention. The list encompasses all of the described fluorescent components of the additive composition including an inherent or intrinsic fluorescent component, an inert fluorescent tracer, or a component that is reacted to become fluorescent.

TABLE 8

| Excitation Range | Emission Range |
|---|---|
| Ultraviolet light | Ultraviolet light |
| Ultraviolet light | Visible light |
| Visible light | Visible light |
| Visible light | Near infrared light |
| Near infrared light | Near infrared light |

It should be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The claimed invention is:

1. A method of monitoring and regulating concentration of corrosion inhibitor and denaturant in fuel ethanol, the method comprising:
   combining corrosion inhibitor and inert fluorescent tracer to provide a traced corrosion inhibitor comprising a corrosion inhibitor-to-inert fluorescent tracer proportion;
   combining the traced corrosion inhibitor and denaturant to provide a traced corrosion inhibitor-denaturant mixture comprising a traced corrosion inhibitor-to-denaturant proportion;

measuring a fluorescent signal of the inert fluorescent tracer in the traced corrosion inhibitor-denaturant mixture and adjusting the traced corrosion inhibitor-to-denaturant proportion as needed to control dosage of denaturant;

dosing the traced corrosion inhibitor-denaturant mixture into fuel ethanol to form treated fuel ethanol;

measuring a fluorescent signal of the inert fluorescent tracer in the treated fuel ethanol;

determining the concentration of the corrosion inhibitor and the denaturant in the treated fuel ethanol based upon the measured fluorescent signal of the inert fluorescent tracer in the treated fuel ethanol; and adjusting the dosing of the traced corrosion inhibitor-denaturant mixture as needed into the fuel ethanol;

wherein the inert fluorescent tracer is Rhodamine B base and the corrosion inhibitor comprises an organic acid anhydride.

2. The method of claim 1, wherein method is operated over a network comprising at least one sensor, controller, digital storage medium, and/or communication means.

3. The method of claim 1, further comprising combining at least a portion of the treated fuel ethanol with gasoline, thereby forming a fuel ethanol composition.

4. The method of claim 3, wherein the fuel ethanol composition ranges from about E10 to about E95.

5. The method of claim 4, further comprising determining total ethanol content in the fuel ethanol composition via fluorometric measurement of the fluorescent signal of the inert fluorescent tracer present in the fuel ethanol composition.

6. The method of claim 1, wherein the corrosion inhibitor further comprises at least one of a monomer organic fatty acid, a dimer organic fatty acid, a trimer organic fatty acid, a tertiary organic amine, an organic (cyclohexyl-containing) amine, and an organic solvent.

7. The method of claim 1, wherein the corrosion inhibitor further comprises an organic solvent selected from an alcohol, a xylene, and a combination thereof.

8. The method of claim 1, wherein the denaturant is a condensate from natural gas condensate.

9. The method of claim 8, wherein the condensate from natural gas condensate is selected from gasoline, methanol, a straight-chain hydrocarbon, naphthalene, an aromatic, and a combination thereof.

10. The method of claim 1, wherein the treated fuel ethanol comprises 1.96% to 4.76% (volume/volume) denaturant.

11. The method of claim 1, wherein the traced corrosion inhibitor-to-denaturant proportion is 1 part traced corrosion inhibitor to 51.9 parts (by weight/weight) of denaturant.

12. The method of claim 1, wherein the measuring steps are performed continuously.

13. The method of claim 1, wherein the measuring steps are performed intermittently.

14. The method of claim 8, wherein the condensate from natural gas condensate is gasoline.

15. The method of claim 8, wherein the condensate from natural gas condensate is methanol.

16. The method of claim 8, wherein the condensate from natural gas condensate is a straight-chain hydrocarbon.

17. The method of claim 8, wherein the condensate from natural gas condensate is naphthalene.

18. The method of claim 8, wherein the condensate from natural gas condensate is an aromatic.

19. The method of claim 1, wherein the corrosion inhibitor further comprises a tertiary organic amine.

* * * * *